United States Patent [19]

Watson

[11] 4,266,669
[45] May 12, 1981

[54] ANESTHESIOLOGISTS INSTRUMENT TRAY

[76] Inventor: Robert L. Watson, 14312 Piccadilly Rd., Silver Spring, Md. 20906

[21] Appl. No.: 98,172

[22] Filed: Nov. 28, 1979

[51] Int. Cl.³ .................. B65D 1/36; B65D 85/00; A61B 15/00
[52] U.S. Cl. .................. 206/564; 206/370; 206/570; 5/436; 5/442; 269/322; 220/20; 220/23.8; 229/28 R
[58] Field of Search .............. 206/564, 557, 363, 370, 206/223, 571; 229/28 R; 220/23.2, 20; 5/341, 436; 269/322; 211/60 T

[56] References Cited

U.S. PATENT DOCUMENTS

| 3,013,656 | 12/1961 | Murphy, Jr. | 206/370 |
|---|---|---|---|
| 3,461,858 | 8/1969 | Michelson | 5/436 |
| 3,638,849 | 2/1972 | Goings | 229/28 R |
| 3,647,104 | 3/1972 | Goings | 220/23.8 |
| 3,650,393 | 3/1972 | Reiss et al. | 206/370 |
| 3,696,920 | 10/1972 | Lahay | 206/363 |
| 3,776,387 | 12/1973 | Brent | 211/60 T |
| 3,802,555 | 4/1974 | Grasty et al. | 206/223 |
| 4,085,845 | 4/1978 | Perfect | 206/564 |
| 4,149,635 | 4/1979 | Stevens | 206/370 |
| 4,160,505 | 7/1979 | Rauschenberger | 206/571 |

Primary Examiner—William T. Dixson, Jr.
Attorney, Agent, or Firm—Roylance, Abrams, Berdo & Farley

[57] ABSTRACT

An inexpensive, disposable tray for anesthesiological use is formed with a central compartment for receiving the patient's head, preferably on a supporting cushion, and arrangements of compartments and recesses on opposite sides of the central compartment to hold specific instruments and medications used during anesthesia in an ordered array according to the sequence in which such articles are employed. The tray is dimensioned to fit across the end of an operating table. Projections along one edge support a suction tube and a manometer.

6 Claims, 5 Drawing Figures

ANESTHESIOLOGISTS INSTRUMENT TRAY

This invention relates to an apparatus which is intended for use in an operating room during medical procedures such as surgery and in particular to an instrument- and medication-holding tray for use by an anesthesiologist.

BACKGROUND OF THE INVENTION

Anesthetic morbidity associated with the induction of general anesthesia and developing during local anesthetic procedures relates both to errors of omission by the anesthetic team and to hastily committed mistakes.

When an anesthesiologist is performing his function during a medical procedure in an operating room and is administering anesthetic to a patient and then monitoring the patient's vital signs, it is customary for him or her to be positioned at the head end of the operating table adjacent the head of the patient. Various instruments, including endotracheal tubes, laryngoscopes, syringes and airways are required from time to time by the anesthesiologist, the syringes containing various chemicals and medications, and these are commonly placed on a cart or table to the right or left of the anesthesiologist, within reach, preferably in a neat and orderly array so that the article needed can be obtained quickly.

Speed can be a very important factor during surgery, and particularly the quickness with which the anesthesiologist can obtain the needed instrument or medication because he or she is usually without assistance and must continuously engage in life support activity. It is not unusual, for example, for the anesthesiologist to be manually operating a ventilator which "breathes" for the patient because certain anesthetic drugs temporarily impair or eliminate the patient's ability to breathe for himself while under the influence of the drug. This ventilating action must not only be continued at a steady rate but that rate must be adjusted, depending on the progress of the surgery and the patient's condition.

Clearly, this requires the anesthesiologist's full attention and it is quite a serious disadvantage for him to need to look away from the patient and reach for what he needs, especially when the need for an instrument or medication is most likely to arise because of an adverse change in the patient's condition, a time when the full and undivided attention of the anesthesiologist can be most critically needed.

Past published anesthetic history is replete with patient catastrophes occurring as a result of anesthetic misadventures during the induction and eduction of anesthesia. These misadventures usually result from problems related to the airway (i.e., upper airway obstruction due to lingual and paraglottic tissue relaxation, laryngospasm, esophageal intubation, tracheal aspiration of gastric contents, etc.).

The errors of omission are preventable and include:

1. Failure to assure a functional suction (vacuum) source close to the patient and anesthetist.
2. Lack of a "backup" laryngoscope blade.
3. Forgotten upper airway devices such as nasal and oral airways of appropriate sizes.
4. Misplacement of endotracheal tubes and lack of backup tubes with attached inflation syringes.
5. Forgotten blood pressure manometers.
6. Misplacement of aligned and labeled anesthetic drugs.
7. Proper head and neck positioning for tracheal intubation.

This problem has been recognized in practice and some anesthesiologists have resorted to makeshift solutions such as placing selected instruments on the surgical drape over the patient's chest or on the table areas which may be unoccupied. These solutions are, however, not regarded as being satisfactory because those areas are not necessarily sterile and because of the probability that a tool will fall from one of these irregular or smooth surfaces to the floor, requiring that a replacement be obtained, and also because it is very difficult to have any organization to the arrangement in the rather limited and miscellaneous spaces used.

Anyone familiar with the operating room setting can remember at least one incident where anesthetic misadventures on induction were followed by a flurry of opening drawers, scattering of nonfunctional laryngoscope blades, and searching for suction adaptors, airways and drugs. The tragic descriptive triad "vomited, aspirated and died" speaks for itself and is followed by increased awareness for a short period of time but all too soon is forgotten in the rapidly moving, complex and sometimes monotonous daily world of the operatory.

similar problems along with some rather different and more general problems associated with storage, shipping and use of medical tools and medications, have been considered by prior art workers, the results being seen in various U.S. patents of which the following are examples.

U.S. Pat. No. 3,013,656; Murphy, Jr.
U.S. Pat. No. 3,650,393; Reiss et al
U.S. Pat. No. 3,696,920; Lahay
U.S. Pat. No. 3,776,387; Brent
U.S. Pat. No. 3,802,555; Grasty et al
U.S. Pat. No. 4,085,845; Perfect
U.S. Pat. No. 4,149,635; Stevens
U.S. Pat. No. 4,160,505; Rauschenberger A similar problem is treated by Brent, but the solution presented is not a fully satisfactory one because of some elements of risk involved and because the Brent device is useful in holding only those articles having a major portion made of a ferrous material.

BRIEF SUMMARY OF THE INVENTION

An object of the present invention is to provide a device which can be placed on an operating table for receiving a patient's head and for providing receptors for instruments and materials to be used to support anesthetic induction at the sides of the patient's head so that the instruments and materials are readily and conveniently available to an anesthesiologist without distracting his or her attention from care of the patient.

A further object is to provide such a device which can be manufactured quite inexpensively and which is disposable after one or a relatively few uses.

Another object is to provide such a device which is formed with recesses or compartments shaped to receive specific instruments and materials in a predetermined arrangement so that they are in the same array each time, so that all airway supportive devices are in the sequential order of use, and so that with minimal familiarization, the anesthesiologist can reach immediately to the same place each time for a needed article.

Briefly described, the invention includes an apparatus for operating room use by an anesthesiologist during surgical procedure comprising an elongated generally rectangular tray having a long dimension approximating the width of an operating table, said tray being placeable on and at the head end of an operating table, wall means extending transversely of said long dimension and forming a part of said tray for dividing said tray into three major portions including a central portion for receiving the head of a patient placed on the operating table, and first and second end portions, at least one of said end portions having a plurality of interior wall means for separating said end portion into a plurality of upwardly opening recesses and compartments having predetermined shapes for receiving specified instruments and medication carriers.

In order that the manner in which the foregoing and other objects are attained in accordance with the invention can be understood in detail, reference is made to the following drawings which form a part of this specification and wherein.

Figure 4:
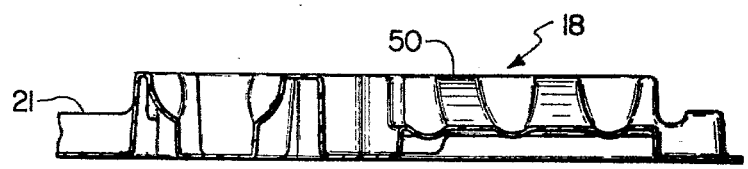
Figure 5:
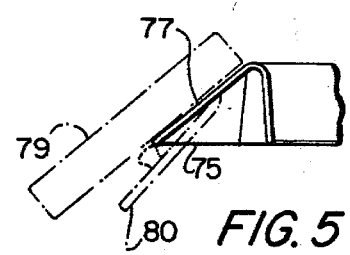
Figure 3:
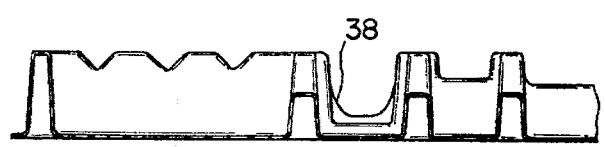
Figure 2:
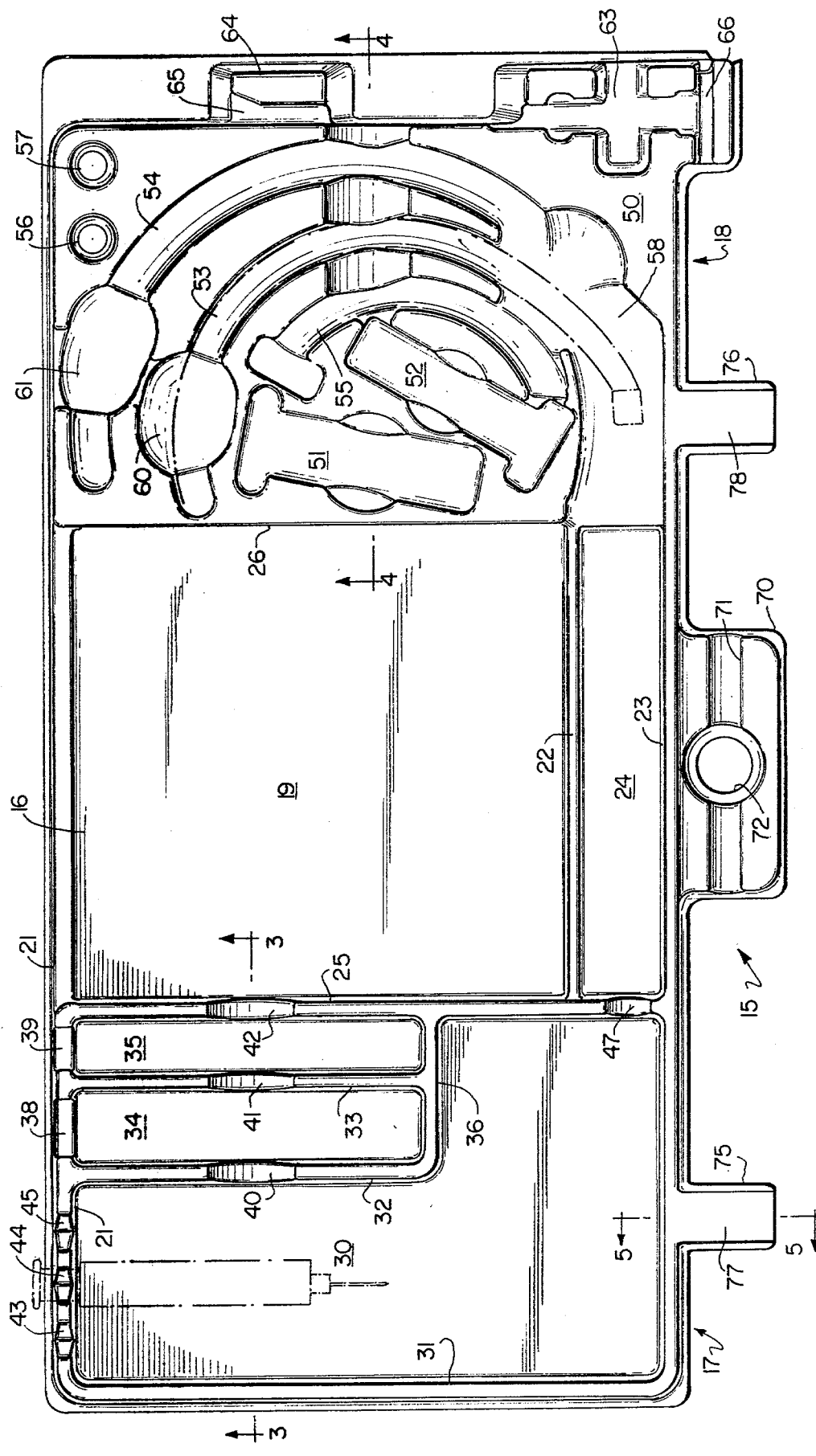
FIG. 2 is a top plan view of an apparatus in accordance with the invention.

FIGS. 3 and 4 are front elevations, in section, along lines 3—3 and 4—4, respectively, of FIG. 2; and FIG. 5 is a partial sectional view along line 5—5 of FIG. 2.

Figure 1:
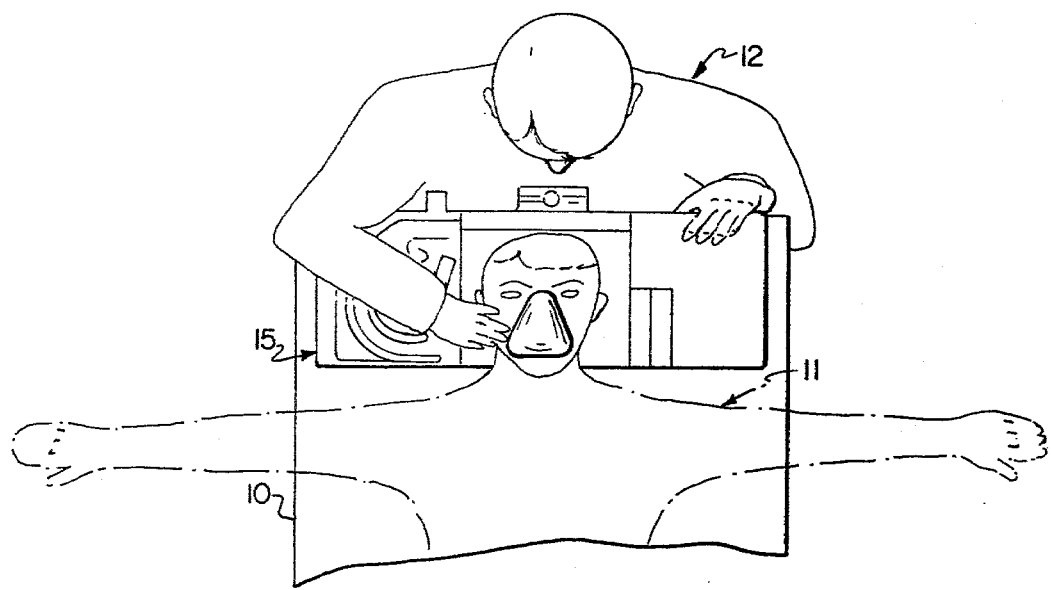
FIG. 1 is a schematic top plan view of an operating table showing the relative positions of a patient, an apparatus in accordance with the invention and an anesthetist.

FIG. 1 is included so that the placement and utility of the device of the present invention can be clearly understood. As shown therein, an operating table 10 supports a patient 11 who will be the subject of a surgical procedure. An anesthetist or anesthesiologist 12 normally is located at the head end of the table 10, standing or seated on a stool, in which position he can administer anesthetics as necessary, accomplish tracheal intubation and airway support, monitor the condition of the patient and perform whatever life support or other functions are necessary. No effort has been made to show the various monitoring instruments which are used by the anesthesiologist nor the other equipment which is generally located near the table, which instruments and equipment form no part of the present invention.

In performing his functions, the anesthesiologist uses various instruments and materials, including medications. In accordance with the invention, a tray indicated generally at 15 is placed on the head end of the operating table with a central portion thereof under the head of the patient and with end portions for receiving the required devices in an ordered, unique and functional array.

As best seen in FIG. 2, the tray is in the shape of an elongated rectangle and is designed to be placed with the longer dimension extending across the width of the operating table. Tray 15 includes transverse wall or partition means dividing the tray into three major portions including a central portion 16 and left and right (as viewed by the anesthesiologist) end portions 17 and 18. Central portion 16 has a major cavity 19 dimensioned to receive the patient's head and can also receive a head support cushion such as that shown in copending U.S. patent application Ser. No. 098,180, filed Nov. 28, 1979 by the present inventor and entitled SUPPORT CUSHION. Thus, the major cavity 19 is preferably almost square and about 20 cm. on a side. A relatively low wall 21, about 13 mm. in height, passes under the patient's neck.

On the opposite side of cavity 19 is a similarly low wall 22 which is parallel with a higher marginal wall 23, those two parallel walls defining a cavity 24. Wall 23 is the same height as the highest (or thickest) portions of the entire apparatus, about 26 mm.

To the left and right, cavities 19 and 24 are bounded by transverse walls 25 and 26, respectively, these being the walls which divide the tray into its three major portions.

End portion 17 includes a relatively large generally L-shaped cavity 30 which is bounded by a continuation of marginal wall 23, part of wall 25, a continuation of wall 21 and an end wall 31, walls 21, 23 and 31 being of the same height as wall 25. The indentation of the L is formed by two walls 32 and 33 which, together with the remainder of wall 25, form two smaller cavities 34 and 35 which are closed at one end by wall 21 and at the other by a relatively short wall 36. The portion of wall 21 at the end of cavities 34 and 25 is provided with indentations 38 and 39, indentation 38 at the end of cavity 34 being relatively deep and extending down almost to the bottom of the tray as will be seen in FIG. 3. Indentation 39 is somewhat shallower. Also, walls 32, 33 and 25 are provided with arcuate indentations 40, 41 and 42 which are aligned with each other, these indentations extending to approximately half the height of the wall. Cavity 34 is to receive a laryngoscope blade attached to a laryngoscope handle in the folded condition with the blade uppermost, recess 38 receiving the hinged end of the laryngoscope so that the blade can readily be grasped and lifted, swinging the illumination portion of the laryngoscope upwardly into the position for use. Cavity 35 is narrower and is intended to receive an extra laryngoscope blade. Indentations 40, 41 and 42 are provided to permit the anesthesiologist's fingers to engage the sides of the blade, as necessary.

The purpose of cavity 30 is to provide a receptacle for the syringes containing the sedative, paralytic and anesthetic medications conventionally used in the anesthetic induction procedure, such an pentathol, succinylcholine and curare, respectively. Thus, the portion of wall 21 forming one end of cavity 30 is provided with indentations 43, 44 and 45 into which the reduced end portions of the syringe plungers can be placed. The syringes themselves will then lie in cavity 30 in a direction generally parallel with wall 31, one such syringe being schematically shown in phantom lines. The syringe can, of course, simply be placed in cavity 30 in sequence.

The remainder of cavity 30 is not devoted to a specific instrument but can be used to hold extra syringes of medications suitable for a particular case or can be used for an anesthesia mask if a mask is to be employed with a specific patient.

Cavity 24 is to receive an inflation syringe which will be used with a pilot balloon on an endotracheal tube. The function and attachment thereof will be described in connection with end 18 of the tray, but it will be observed that the portion of wall 25 at one end of cavity 24 is provided with an indentation 47 across which the end of the inflation syringe can lie.

Turning now to end portion 18, it will be observed from FIG. 2 and the sectional view of FIG. 4 that portion 18 has an upper surface 50 which lies in the same plane as the upper edges of walls 23, 25, 26 and 31 and that several recesses are formed therein to receive specific components. These include generally T-shaped recesses 51 and 52; relatively long arcuate recesses 53 and 54; a somewhat smaller arcuate recess 55; and two cylindrical recesses 56 and 57. Recesses 51 and 52 are each provided with arcuate indentations at approximately their midpoints and are designed to receive, respectively, large and medium size oral airways. Recess 55 is to receive a nasal airway, and recesses 53 and 54 are to receive endotracheal tubes. The oral airways are used both as bite blocks and as a means of clearing the upper airway by means of moving the tongue forward and away from the glottis. The nasal airway may or may not be used, depending upon circumstances, but is frequently used in those conditions where paralysis has caused collapse of soft oral tissue, and the mouth cannot be opened precluding effective use of the oral airways.

The curvature of arcuate cavities 53 and 54 deserves special comment because the curvature illustrated is selected to contribute to the effective use of the endotracheal tubes. Generally speaking, endotracheal tubes are supplied with a curvature in accordance with an international standard, but it has been found in practice that the curvature is not completely correct for convenient insertion following visualization and opening of the passage by the laryngoscope. It has therefore become common practice for physicians to use supplementary techniques, such as the insertion of a malleable wire in the tube, to modify the curvature of the tube before insertion, after which the wire is extracted. Cavities 53 and 54 are constructed with the desired ultimate curvature so that the insertion of such a wire is no longer necessary. Thus, placing the endotracheal tube in cavity 53 or 54 for a relatively short interval of time imparts to that tube the desired practical curvature, enabling immediate use without further modification.

It will also be observed that arcuate cavities 53 and 54 merge into a relatively large open cavity 58 near wall 23. The end of the tubes terminate in that region, one of the tubes being connected to the inflating syringe, previously mentioned, which is disposed in cavity 24. The syringe, normally a 10 cc. syringe, is pre-attached to the pilot balloon of the endotracheal tube when it is placed in the tray so that the tube is completely suited for use.

As is well known, endotracheal tubes can be provided with a pilot balloon near the insertion end thereof so that, after insertion, the balloon can be inflated, blocking the passage and providing full control of breathing by the physician or, as is often necessary, preventing trachael aspiration of gastric contents. When placed in cavities 53 or 54, the balloon portion will rest in the enlarged portions 60 or 61 of those cavities, near the insertion end of the tube. However, cavities 60 and 61 are made somewhat larger than necessary to accommodate the inflation type of balloon because a form of endotracheal tube having an expandable foam balloon, which is expanded in its relaxed state, is also coming into use. That form of endotracheal tube also uses a syringe, but uses that syringe as a deflation device, delfating the normally expanded balloon until after insertion, whereupon venting permits the balloon to expand in the passage.

Cavities 56 and 57 are provided to receive fittings or adaptors which are sometimes used for endotracheal tubes of different sizes.

At the right-hand end of the tray structure there is provided a cavity 63 of relatively complex design, and having a cross-shape at one end. A projection at one corner of the tray is formed with a transverse slot 66. Further along the end of the tray is a support shoulder 64 having a recess 65 which cooperates the recess 63. These recesses are to receive a laryngo-tracheal sprayer which is a form of spray syringe commonly used for injecting a local anesthetic for the purpose of minimizing involuntary reactions of the patient's body during intubation. The syringe portion fits in cavity 63 and the relatively long extension of the spray tube extends away from the anesthesiologist and rests in support cavity 65, protruding beyond that support surface over the lateral flange at the bottom of the tray. The end of the plunger rests in slot 66 and is maintained in its partially withdrawn position by the intervening space. Thus, the sprayer is completely prepared for use.

At the middle of the tray, and on the side toward the anesthesiologist, is a rectangular projection 70 having a longitudinal semicircular slot 71 and a hole 72 at the center thereof. This projection is formed so that it can project beyond the end of the operating table to receive a suction tube. It often occurs during anesthetic procedures that material such as gastric fluids suddenly enter the regions of the mouth or pharynx and, if permitted to remain, particularly in the absence of an occluding device such as the inflated cuff of the endotracheal tube, can be drawn into the lungs causing aspiration with various adverse consequences including death. The condition arises most often during insertion or removal of the tube or laryngoscope. Thus, it is desirable, and is common practice to have a suction tube, with a Tonsil or Yankeur suction tip thereon, attached to a conventional vacuum suction, in operation.

The purpose of projection 70 is to provide a convenient location to support the suction hose and tip in any of several possible ways. The tube can simply be laid across the projection, resting in slot 71. Alternatively, the tip can be inserted from above through hole 72. Or, if the anesthesiologist prefers to stop the possibly annoying sound of air being continuously drawn into the tip, the hose near the tip can be bent double and pushed upwardly into hole 72 wherein it will remain ready for use.

Finally, on either side of projection 70 are projections 75 and 76 having sloping surfaces 77 and 78, respectively. As best seen in FIG. 5, surface 77 slopes outwardly and downwardly, the projection being hollow so that a manometer 79 of the type having a back clip 80 can be attached to the projection. So attached, the manometer is slanted at a convenient angle for periodic observation to check the blood pressure of the patient as is periodically necessary. The projections are provided on both sides so that the pressure can be monitored using either of the patient's arms.

As illustrated, the tray can be formed from a polymeric material by conventional vacuum forming techniques so that it is inexpensive and disposable. Thus formed, the tray walls and the portion beneath surface 50 are hollow and the tray is light but quite sturdy.

It is particularly significant to note the order in which the medications and instruments are most likely to be used and to compare that order with the arrangement of articles in the tray compartments. Although not all instruments are used with every patient, if used they would be required in the following sequence.

mask
pentathol syringe (or other sedative)
succinylcholine syringe (or substitute)
curare syringe (or substitute)
nasal or oral airway
suction (vacuum)—any time laryngoscope
laryngo-tracheal sprayer
endotracheal tube and inflation syringe
B. P. Manmometer (any time)

The backup laryngoscope blade, extra endotracheal tube, and suction tube are, of course, available as needed, and the manometer is noted periodically. Generally, however, the devices are used from the outside in toward the patient, a completely logical and practical arrangement.

While one advantageous embodiment has been chosen to illustrate the invention it will be understood by those skilled in the art that various changes and modifications can be made therein without departing from the scope of the invention as defined in the appended claims.

What is claimed is:

1. An apparatus for operating room use by an anesthesiologist during surgical procedures comprising
    an elongated generally rectangular tray having a long dimension approximating the width of an operating table, said tray being placeable on and at the head end of an operating table;
    wall means extending transversely of said long dimension and forming a part of said tray for dividing said tray into three major portions including
        a central portion for receiving the head of a patient placed on the operating table, and
        first and second end portions,
    at least one of said end portions having
        a plurality of interior wall means for separating said end portion into a plurality of upwardly opening recesses and compartments having predetermined shapes for receiving specified instruments.

2. An apparatus according to claim 1 wherein each of said end portions has a plurality of interior wall means for separating said end portion into a plurality of upwardly opening recesses and compartments having predetermined shapes for receiving specified instruments.

3. An apparatus according to claim 2 wherein said tray includes
    a projecting portion extending from one longer side thereof and having an opening for receiving a suction tube when said tray is so oriented that said one longer side is adjacent the end of the operating table and said projecting portion extends beyond said table end.

4. An apparatus according to claim 3 and including a second projecting portion extending from said longer side and having an inclined member for supporting a manometer.

5. An apparatus according to claim 3 wherein one of said end portions includes recesses shaped to receive at least one endotracheal tube, at least one oral airway and at least one nasal airway and with a curvature for the endotracheal tube which fixes the curvature of the plate tube in such a way that it is optimally curved for passage into the trachea without the aid of a stylet wire.

6. An apparatus according to claim 5 wherein the other of said end portions includes a compartment for receiving a laryngoscope.

* * * * *